US010195190B2

(12) United States Patent
Brem et al.

(10) Patent No.: US 10,195,190 B2
(45) Date of Patent: Feb. 5, 2019

(54) LOCAL DELIVERY FORMS OF ACRIFLAVINE FOR TREATING TUMORS

(71) Applicant: The Johns Hopkins University, Baltimore, MD (US)

(72) Inventors: Henry Brem, Ownings Mills, MD (US); Antonella Mangraviti, Baltimore, MD (US); Alessandro Olivi, Baltimore, MD (US); Betty M. Tyler, Catonsville, MD (US); Tula Raghavan, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/549,547

(22) PCT Filed: Feb. 11, 2016

(86) PCT No.: PCT/US2016/017493
§ 371 (c)(1),
(2) Date: Aug. 8, 2017

(87) PCT Pub. No.: WO2016/130767
PCT Pub. Date: Aug. 18, 2016

(65) Prior Publication Data
US 2018/0036301 A1 Feb. 8, 2018

Related U.S. Application Data

(60) Provisional application No. 62/114,652, filed on Feb. 11, 2015.

(51) Int. Cl.
*A61K 31/473* (2006.01)
*A61K 9/00* (2006.01)
*A61K 31/4188* (2006.01)
*A61K 47/34* (2017.01)

(52) U.S. Cl.
CPC .......... *A61K 31/473* (2013.01); *A61K 9/0024* (2013.01); *A61K 31/4188* (2013.01); *A61K 47/34* (2013.01)

(58) Field of Classification Search
None
See application file for complete search history.

(56) References Cited

U.S. PATENT DOCUMENTS

| 4,861,627 A | 8/1989 | Mathiowitz |
| 5,019,400 A | 5/1991 | Gombotz |
| 5,891,864 A * | 4/1999 | Han ............... A61K 31/708 514/297 |
| 6,262,034 B1 | 7/2001 | Mathiowitz |
| 6,491,666 B1 | 12/2002 | Santini, Jr. |
| 6,527,762 B1 | 3/2003 | Santini, Jr. |
| 6,976,982 B2 | 12/2005 | Santini, Jr. |
| 7,226,442 B2 | 6/2007 | Sheppard, Jr. |
| 7,604,628 B2 | 10/2009 | Santini, Jr. |

FOREIGN PATENT DOCUMENTS

| CN | 103933044 | 7/2014 |
| WO | 9321906 | 11/1993 |

OTHER PUBLICATIONS

Alfarouk, et al, "Glycolysis, tumor metabolism, cancer growth and dissemination. A new pH-based etiopathogenic perspective and therapeutic approach to an old cancer question", Oncoscience 1(14):777-802 (2014).
Beck et al., "A New Long-Acting Injectable Microcapsule System for the Administration of Progesterone," Fertil. Steril., 31:545-51 (1979).
Benita, et al., "Characterization of Drug-Loaded Poly( d,Z-lactide) Microspheres"J. Pharm. Sci., 73:1721-4 (1984).
Bertout, et al., "HIF2alpha inhibition promotes p53 pathway activity, tumor cell death, and radiation responses", PNAS, 106:14391-6 (2009).
Can and Kaplan, "Synthesis, characterization and in vitro antibacterial assessments of a novel modified poly[maleic anhydride-alt-a-acrylic acid]/acriflavine conjugate", Polymer Bulletin, 71(11):2903-21 (2014).
Castro, et al., "Current and future strategies for the treatment of malignant brain tumors", Pharmacol. Ther. 98(1):71-108 (2003).
Chang, et al., "Patterns of care for adults with newly diagnosed malignant glioma", JAMA, 293(20):557-64 (2005).
Fan, et al., "Acriflavine suppresses the growth of human osteosarcoma cells through apoptosis and autophagy", Tumour Biol., 35(10):9571-6 (2014).
Foersch, et al., "Confocal Laser Endomicroscopy for Dagnosis and Histomorphologic Imaging of Brain Tumors In Vivo", PLoS. ONE, 7(7):e41760 (2012).

(Continued)

*Primary Examiner* — Bong-Sook Baek
(74) *Attorney, Agent, or Firm* — Pabst Patent Group LLP

(57) ABSTRACT

Local delivery formulations of the antineoplastic and microbicide agent acriflavine, and methods of making and using thereof are significantly more efficacious at increasing the median survival of subjects with proliferative disease than systemic administrations of acriflavine. The local delivery formulations of acriflavine show a dose-dependent increase in the median survival of subjects. The local delivery forms provide the increased efficacy without the toxicity associated with systemic administration of the agent.

5 Claims, 3 Drawing Sheets

(56) References Cited

OTHER PUBLICATIONS

Hassan, et, al., "Novel activity of acriflavine against colorectal cancer tumor cells" Cancer Sci., 102(12):2206-13 (2011).
Judy, et al., "Effectiveness of controlled release of a cyclophosphamide derivative with polymers against rat gliomas." J Neurosurg. 82:481-6 (1995).
Kim, et al., "Resorbable polymer microchips releasing BCNU inhibit tumor growth in the rat 9L flank model", J Control Release., 123(2):172-8 (2007).
Kim, et al., "Suppression of xenobiotic-metabolizing enzyme expression in rats by acriflavine, a protein kinase C inhibitor. Effects on epoxide hydrolase, glutathione S-transferases, and cytochromes p450", Drug Metab Dispos., 28(1):66-72 (1998).
Lee, et al., "Acriflavine inhibits HIF-1 dimerization, tumor growth and vascularization" PNAS, 106 (42):17910-5(2009).
Lee, et al., "Antitumor activity of acriflavine in human hepatocellular carcinoma cells", Anticancer Res., 34(7):3549-56 (2014).
Macia, et al., "Antianglogenic therapy in the squamous cell carcinoma", Intl J Oral Maxillofacial Surg., 42(10):1173-4 (2013).
Martirosyan, et al., "Potential application of a handheld confocal endomicroscope imaging system using a variety of fluorophores in experimental gliomas and normal brain", Neurosurg Focus, 36 (2):E16, (2014).
Mathiowitz et al., "Morphology of polyanhydride microsphere delivery systems," J. Scanning Microscopy, 4:329-40 (1990).
Mathiowitz, et al., "Novel microcapsules for delively systems" Reactive Polymers, 6:275-83 (1987).
Nitiss, "Targeting DNA topolsomerase II in cancer chemotherapy", Nat Rev Cancer, 9(5): 338-50 (2009).
Palvai, et al., "Dual drug loaded vitamin D3 nanoparticle to target drug resistance in cancer", RSC Adv., 4(100):57271-81 (2014).
Raza, et al. "Local delivery of antineoplasti agents by controlled-release polymers for the treatment of malignant brain tumours", Expert Opin. Biol. Ther. 5(4):477-494 (2005).
Recinos, et al., "Combination orf Intracranial Temozolomide With Intracranial Carmustine Improves Survival When Compared With Either Treatment Alone in a Rodent Glioma Model", Neurosurgery, 6:530-7 (2010).
Sipos, et al., "Optimising interstitial delivery of BCNU from controlled release polymers for the treatment of brain tumors", Cancer Chemother Pharmacol., 39(5):383-9 (1997).
West et al., "Drug delivery: Pulsed polymers" Nat Mater., 2(11):709-10 (2003).
International Search Report for corresponding PCT application PCT/US2016/017493 dated Aug. 24, 2017.

\* cited by examiner

LOCAL DELIVERY FORMS OF ACRIFLAVINE FOR TREATING TUMORS

CROSS REFERENCE TO RELATED APPLICATIONS

This application is a 371 application of International Application No. PCT/US2016/017493, filed Feb. 11, 2016, which claims priority to and benefit of U.S. Provisional Application No. 62/114,652 "Acriflavine Biodegradable CCP:SA Polymers for the Treatment of Malignant Glioma" filed on Feb. 11, 2015, the disclosures of which are hereby incorporated herein by reference in their entirety.

FIELD OF THE INVENTION

The invention is generally directed to the field of local drug delivery using local delivery forms. The drugs are delivered locally, at high concentrations, to avoid systemic spread of the drug.

BACKGROUND OF THE INVENTION

It is estimated that nearly 23,400 new cases of primary malignant brain and central nervous system (CNS) tumors will be diagnosed in the United States in 2014; of those, approximately 2,240 will be diagnosed in children ages 0 to 14 years and 540 will be diagnosed in adolescents ages 15 to 19 years. Overall mortality rates have not changed significantly in the past decade. Both incidence and mortality rates are higher for whites than for people of other racial/ethnic groups. In all racial/ethnic groups, men have higher incidence and mortality rates than women. Brain tumors are the leading cause of death from solid tumor cancers in children. Brain and CNS tumors make up approximately 21 percent of all childhood cancers. The incidence rate of brain and CNS cancers in children has been relatively stable since the mid-1980s, but the death rate has dropped over this period.

The causes of most brain and CNS cancers are not known. However, factors that may increase the risk of developing certain types of brain tumors include exposure to radiation, exposure to vinyl chloride, and having certain genetic syndromes. There are no screening tests for brain and CNS cancers. Standard treatments for adult brain cancer include watchful waiting, surgery, radiation therapy, chemotherapy, and targeted therapy. Newer treatments for adult brain cancer, such as biological therapy and proton beam radiation therapy are being studied in clinical trials. Assuming that incidence and survival rates follow recent trends, it is estimated that $4.9 billion will be spent on brain cancer care in the United States in 2014.

Chemotherapy is a cancer treatment that uses drugs to stop the growth of cancer cells, either by killing the cells or by stopping them from dividing. When chemotherapy is taken by mouth or injected into a vein or muscle, the drugs enter the bloodstream and can reach cancer cells throughout the body (systemic chemotherapy). When chemotherapy is placed directly into the cerebrospinal fluid, an organ, or a body cavity such as the abdomen, the drugs mainly affect cancer cells in those areas (regional chemotherapy). Combination chemotherapy is treatment using more than one anticancer drug. To treat brain tumors, a wafer that dissolves may be used to deliver an anticancer drug directly to the brain tumor site after the tumor has been removed by surgery. The way the chemotherapy is given depends on the type and grade of tumor and where it is in the brain.

Anticancer drugs given by mouth or vein to treat brain and spinal cord tumors cannot cross the blood-brain barrier and enter the fluid that surrounds the brain and spinal cord. Instead, an anticancer drug is injected into the fluid-filled space to kill cancer cells there. This is called intrathecal chemotherapy.

Local, sustained drug release using biodegradable polyanhydride poly-(1,3 bis[p-carboxyphenoxy] propane-co-sebacic acid, or p[CPP:SA, 20:80], improves the anti-glioma efficacy of some chemotherapeutic agents for treatment of brain tumors. P[CPP:SA, 20:80] is an FDA-approved method of local drug delivery that has been shown to be biocompatible in the brain with no evidence of systemic or local toxicity and is currently clinically used for the local delivery of BCNU (GLIADEL®). Despite vast improvements in overall survival rates in systemic cancers, primary brain malignancies still have some of the worst 5-year survival rates among all human cancers (Macmillan Cancer Support. Living after diagnosis—median cancer survival times: An analysis of London School of Hygiene and Tropical Medicine, 2011).

There remains a need for efficacious treatments to extend the median survival of subjects with brain tumor or other solid tumors.

Therefore, it is an object of the present invention to provide local delivery forms of chemotherapeutics for treatment, prophylaxis, or management of proliferative diseases.

It is another object of the present invention to provide methods of making the local delivery formulations.

It is yet another object of the present invention to provide methods of using the local delivery forms of local delivery formulations.

SUMMARY OF THE INVENTION

Compositions containing biocompatible polymeric local delivery forms of acriflavine (ACF) or derivatives or salts thereof are administered to an individual in need of treatment. Typically, the subject in need of treatment has cancer with primary tumors, de novo tumors, secondary tumors, or tumor metastases. The tumors are typically solid tumors, such as sarcomas, carcinomas, and lymphomas. In preferred embodiments, the tumors to be treated are brain tumors or tumors of the central nervous system.

Typically, the composition contain acriflavine or its derivatives in a local delivery form for sustained local administration of an effective amount of the acriflavine or its derivatives to reduce tumor size, prolong survival of the subject, and/or reduce systemic side effects in the subject. The local delivery form is typically in the form of a polymeric implant, particles, or a microchip. The composition has reduced systemic side effects in the subject in severity, length of time, or in number of side effects as compared to the acriflavine administered in solution.

In some aspects, the local delivery form is a polymer containing acriflavine or its derivatives at a concentration of between about 10% and 70% by weight. Preferably, the local delivery form is a polymer containing acriflavine or its derivatives at a concentration of between about 20% and 60% by weight. More preferably, the local delivery form is a polymer containing acriflavine or its derivatives at a concentration of about 50% by weight.

In some embodiments, the composition may further include temozolomide or other chemotherapeutic agents.

The composition may be administered to the subject at an area close to the tumor, or at an area of a resected tumor.

In an experimental glioma model, the intracranially implanted local delivery forms of acriflavine extended the survival of 100% or 50% of all the treated animals to 300 days depending on the % of drug in the polymer, whereas treatment groups receiving acriflavine systemically, or daily oral doses of temozolomide, succumbed to tumor within 40 days.

DETAILED DESCRIPTION OF THE INVENTION

I. Definitions

Figure 1:
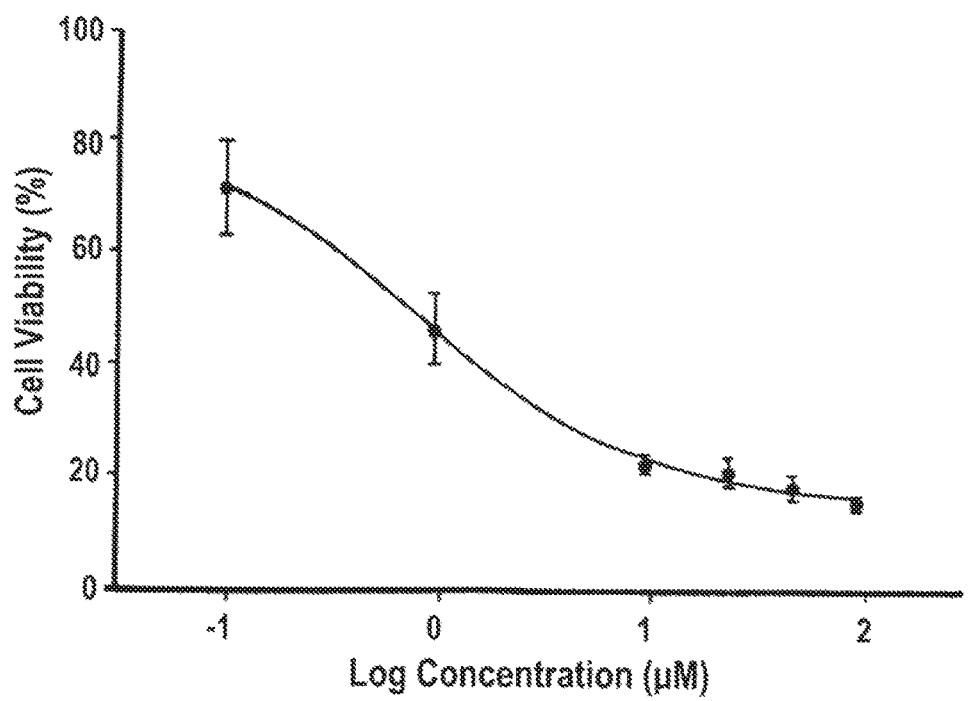
FIG. 1 is a line graph of 9 L rat gliosarcoma cell viability (%) at different concentrations of ACF. The IC50 concentration of ACF was found to be 1.07 µM on 9 L rat glioma cells.

As used herein, "local" therapy refers to therapy placed locally either surgically, via a needle or through a vessel or subcutaneously, or intramuscularly, or intraperitoneally.

As used herein, the term "local delivery form" refers to patches, discs (wafers), rods, microchips, or particulates enclosing, encapsulating or impregnated with active agent (s), and/or active agent formulation(s). The local delivery forms are placed at a desired site in a subject's body and release the agent(s) locally in a dosage not sufficient to cause systemic efficacy or side effects.

As used herein, "extended release" or "sustained release" refers to a therapeutically effective amount of active agent being released over a period of time ranging from days, weeks, months to years. Typically, release will be achieved over a period of one or more weeks following implantation.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can range from between hours and weeks.

As used herein the term "effective amount" or "therapeutically effective amount" means a dosage sufficient to treat, inhibit, or alleviate one or more symptoms of a disease state being treated or to otherwise provide a desired pharmacologic and/or physiologic effect. The precise dosage will vary according to a variety of factors such as subject-dependent variables (e.g., age, immune system health, etc.), the disease or disorder, and the treatment being administered. The effect of the effective amount can be relative to a control. Such controls are known in the art and discussed herein, and can be, for example the condition of the subject prior to or in the absence of administration of the drug, or drug combination, or in the case of drug combinations, the effect of the combination can be compared to the effect of administration of only one of the drugs.

As used herein, the term "median survival" refers to the length of time from either the date of diagnosis or the start of treatment for a disease, such as cancer, during which half of the patients in a group of patients diagnosed with the disease are still alive.

As used herein, "efficacy" refers to affecting tumor size or prolonging survival, such as median survival.

The term "pharmaceutically acceptable", as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

A "pharmaceutically acceptable carrier", as used herein, refers to all components of a pharmaceutical formulation which facilitate the delivery of the composition in vivo. Pharmaceutically acceptable carriers include, but are not limited to, diluents, preservatives, binders, lubricants, disintegrators, swelling agents, fillers, stabilizers, and combinations thereof.

As used herein, the term "antineoplastic" refers to any biological compound or substance whose purpose is to reduce, ameliorate, eliminate, or halt the metastasis, migration, or proliferation of a neoplasm.

II. Composition

A. Polymers

Acriflavine is formulated into a polymeric matrix for long term release. The polymers must be biocompatible. Preferably they degrade by hydrolysis although enzymatically degradable polymers may be used. Preferred polymers are synthetic, but may be naturally occurring. Polymers may be homopolymers, copolymers, blends, or block copolymers.

Representative synthetic polymers which can be used to faint the matrix include hydrophobic polymers such as the bioerodible polymers including polyanhydrides, poly(hydroxy acids) and polyesters, as well as blends and copolymers thereof. Representative bioerodible poly(hydroxy acids) and copolymers thereof include poly(lactic acid), poly(glycolic acid), poly(hydroxy-butyric acid), poly(hydroxyvaleric acid), poly(caprolactone), poly(lactide-co-caprolactone), poly(lactide-co-glycolide, polyanhydrides and polyorthoesters, can be used. Additional synthetic polymers include polyphosphazenes, polyamides, polycarbonates, polyacrylamides, polysiloxanes, polyurethanes and copolymers thereof. Additionally, polyvinyl polymers can be used, which, as defined herein includes polyvinyl alcohols, polyvinyl ethers, polyvinyl esters and polyvinyl halides. Exemplary polyvinyl polymers include poly(vinyl acetate), polyvinyl phenol and polyvinylpyrrolidone.

Other polymers which can be incorporated include polyalkylenes such as polyethylene and polypropylene; polyarylalkylenes such as polystyrene; poly(alkylene glycols), such as poly(ethylene glycol); poly(alkylene oxides), such as poly(ethylene oxide); and poly(alkylene terephthalates), such as poly(ethylene terephthalate).

Most preferred polymers are polyanhydrides and polyhydroxy acids, especially poly(lactic acid-glycolic acid) copolymers. These can be selected to provide optimal incorporation and release of drug.

In the preferred embodiment, the polymer is a biodegradable polyanhydride copolymer, poly[bis(p-carboxyphenoxy)propane:sebacic acid] in a 20:80 molar ratio.

B. Therapeutic, Prophylactic and Diagnostic Agents

1. Antineoplastic Agents

Antineoplastic agents include acriflavine (3,6-diamino-10-methylacridinium chloride mixed with 3,6-acridinediamine), a mixture of two closely related acridine molecules, with a structure according to Formula I:

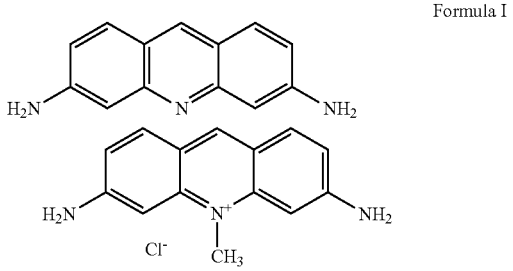

Formula I and derivatives of acriflavine such as proflavin, proflavine hemisulfate, and proflavine hydrochloride, and other prodrugs or salts thereof.

Acriflavine (ACF), a mixture of two closely related acridine molecules, was discovered nearly 100 years ago and has a broad spectrum of clinical applications. ACF is known for its trypanocidal, antibacterial, and antiseptic activity and is mostly used topically for wound healing as well as systemically for gonorrhea treatment via both intravenous and oral administration. Systemic use, however, is extremely limited due to toxicity.

The effects of ACF on cancer cells were first reported 50 years ago, but interest again peaked in 2009, when ACF, out of 336 FDA-approved drugs, was shown to be the most potent hypoxia-inducible factor 1α (HIF-1α) inhibitor. ACF was shown to inhibit HIF-1α transcriptional activity by preventing the dimerization of HIF-1α and HIF-1β, which reduced angiogenic cells mobilization and tumor vascularization and successfully suppressed tumor growth in prostate cancer xenografts (Lee et al, Proc Natl Acad Sci USA, 106 (42):17910-7915(2009)). Recent studies have shown that HIF-1α inhibition is not its only mechanism of action but that ACF can also induce apoptotic and autophagic effects in cancer cells (Fan et al., Tumour Biol; 35(10):9571-9576 (2014)). ACF has demonstrated highly effective antitumor activity against a wide spectrum of cancers (Hassan et al., Cancer Science, 102(12): 2206-213 (2011); Lee et al., Anticancer Res. 34(7):3549-3556 (2014)).

Acriflavine inhibits Vascular Endothelial Growth Factor (VEGF), which is downstream from HIF-1. HIF-1 also helps sustain a glycolytic phenotype, so inhibiting it may also facilitate the switch from glycolysis back to mitochondrial respiration, thwarting the Warburg Effect—the production of energy by high rate of glycolysis followed by lactic acid fermentation in the cytosol (Alfarouk et al, Oncoscience, 1(14):777-802 (2014)). Acriflavine interferes with the binding domain of HIF-2 thereby preventing its downstream angiogenic and glycolytic factors from functioning. Additionally, the inhibition of HIF-2 has been shown to promote the p53 axis, which reduces the glycolytic phenotype (Bertout et al., Proc Natl Acad Sci USA, 106:14391-14396 (2009)).

Acriflavine also inhibits topoisomerases I and II (Hassan et al., Cancer Science, 102(12): 2206-213 (2011)). These enzymes are involved in DNA coiling during replication. Cancer drugs that target topoisomerase II are known to create DNA damage in tumor cells during replication (Nitiss, Nature Reviews Cancer, 9(5); 338-350 (2009)). Acriflavine also inhibits protein kinase c (PKC), which plays a key role in cell proliferation pathways (Kim et al., Drug Metabolism and Disposition, 26(1):66-72 (1998)).

Systemically delivered acriflavine has demonstrated highly effective antitumor activity against a wide spectrum of cancers. Thus far, no study has reported its efficacy in glioma cell lines or brain tumor models. Acriflavine's demonstrated inhibition of Hypoxia Inducible Factors (HIFs) and of topoisomerases makes it a good candidate for treatment of glioblastoma multiforme (GBM). However, one of the major challenges of brain tumor therapy is the unique anatomical and physiological barrier, the blood-brain barrier (BBB), which prevents most chemotherapeutic agents from penetrating the brain in therapeutic doses. ACF has physicochemical and pharmacokinetic characteristics that hamper a high systemic bioavailability as well as a good penetration of the BBB to reach the tumor tissue (Fan et al., Tumour Biol; 35(10):9571-9576 (2014)). Instead, ACF has been used as a rapid-acting fluorescent dye to provide histological information on gliomas and tumor margins in animal models (Martirosyan et al., Neurosurg Focus, 36 (2):E16, (2014)), as well as for diagnoses of intracranial neoplasias (Foersch et al., PLoS ONE, 7(7):e41760 (2012)).

In preferred embodiments, the agent is acriflavine and its derivatives. These are typically provided in a polymeric matrix at a concentration range of between 3% and 70% by weight. In preferred embodiments, the agents are provided at a concentration range of between 5% and 60%.

2. Additional Agents

Other chemotherapeutic agents can be added to the local delivery forms with the antineoplastic agent(s). These typically include alkylating agents, nitrosoureas, and antimetabolites. Specific examples include 5FU, FUDR, cisplatin, carboplatin, doxorubicin, daunorubicins, cytoarabine, cyclophosphamide, paclitaxel, gemcitabine, ifosfamide, camptothecins such as irinotecan, methotrexate, procarbazine, vincristine, and vinblastin.

Temozolomide (Temodar®) capsules, made by Merck & Co., Inc.) is an U.S. Food and Drug Administration approved treatment of adult patients with newly diagnosed GBM concomitantly with radiotherapy (RT) and then as maintenance treatment. Temozolomide (TMZ) previously received accelerated approval in 1999 for the treatment of adult patients with refractory anaplastic astrocytoma. This treatment indication is also converted to full approval based on the results of the GBM study described below.

In a phase III study conducted by the European Organization for Research and Treatment of Cancer (EORTC) in newly diagnosed GBM patients. Median survival was 14.6 months with TMZ and RT treatment versus 12.1 months with RT treatment alone. The local delivery forms disclosed herein may include acriflavine alone, or in combination with TMZ, and may be used to treat GMB. The local delivery forms are able to extend median survival from between 0.1 fold and 100 fold.

Additional agents that may be incorporated with the anti-neoplastic agents in the local delivery forms include be analgesics, anti-convulsants, anti-fibrotic agents, anti-infectives, antibacterials, anti-fungals, anti-thrombotics, anti-inflammatory agents such as TNF-α inhibitors, non-steroidal anti-inflammatory drugs (NSAIDs) such as aspirin and ibuprofen, Jak and/or Stat inhibitors, and NKG2D inhibitors central nervous system stimulants, cholinesterase inhibitors, dopamine receptor agonists, hormones, immunomodulators, immunosuppressives, migraine agents, non-steriodal anti-inflammatory drugs (NSAIDs), nucleoside analogs, anti-neurodegenerative agents (e.g, L-DOPA).

Imaging agents may also be incorporated in the local delivery forms. The imaging agents include one or more radionuclides, optical tracers such as bioluminescent, chemiluminescent, fluorescent or other high extinction coefficient or high quantum yield optical tracers, T1 magnetic resonance imaging (MRI) agents in the class of heavy metals (gadolinium, or dysprosium), T2 contrast agents (iron oxide, or manganese oxide), or iodinated agents.

C. Pharmaceutically Acceptable Carriers

The polymeric formulation or storage container may include one or more pharmaceutically acceptable carriers. Pharmaceutically acceptable carriers include, but are not limited to, diluents, preservatives, binders, lubricants, disintegrators, swelling agents, fillers, stabilizers, and combinations thereof.

III. Methods of Making

Local delivery forms are typically biodegradable polymeric units in a form of an implant such as a rod, disc (wafer), or microchip, or in particulate form, such as microparticle or nanoparticle form. The local delivery forms typically have dimensions suitable for implantation into tissues. For example, discs may have a diameter of between 1 mm and 10 mm and a thickness of between 0.5 mm and 3 mm. The rods may have a length of between 1 mm and 10 mm, and a width of between 0.5 mm and 3 mm.

Nanoparticles and microparticles may generally be of spherical shape, but other shapes are also contemplated. The nanoparticles generally have a diameter of between about 10 nm and 1000 nm, preferably between about 60 nm to about 450 nm. The microparticles generally have a diameter of between about 1 micrometer and 300 micrometer, and preferably between about 20 micrometer and 100.

A. Methods of Making Polymeric Implants

In the preferred embodiment, the drug is homogeneously dispersed in a wafer approximately 1.45 cm in diameter and 1 mm thick. Typically polymer is dissolved in an FDA approved solvent such as methylene chloride, drug added to a desired weight percentage typically between 10 and 90% by weight, more typically between 40 and 70%, and most preferably about 50%, and the product spray dried, solvent cast or die cast to form polymeric implants. Solvent is removed by evaporation, and the resulting implants sealed under nitrogen or another inert gas into a foil or light resistant blister pack.

B. Methods of Making Microparticles

Generally, microspheres have a diameter from the nanometer range up to about 300 microns, most preferably 40-80 microns. The microparticles must have both structural integrity and optimal surface area, including both a crenulated outer surface and a highly porous or trabeculated interior. Porosity of the interior is designed so that internal voids are interconnected to each other and to the microsphere surface prior to injection in the body.

In one embodiment, the microspheres can be fabricated using methods including solvent evaporation, hot-melt microencapsulation or spray drying. Microparticles made of thermoplastic polymers such as polyanhydrides made of bis-carboxyphenoxypropane and sebacic acid or poly(fumaric-co-sebacic) can be prepared by hot-melt or solvent evaporation microencapsulation. Polystyrene and polyhydroxy acid microspheres can be prepared by solvent evaporation. Hydrogel microspheres can be prepared by dripping a polymer solution, such as alginate, chitosan, alginate/polyethylenimine (PEI) and carboxymethyl cellulose (CMC), from a reservoir though microdroplet forming device into a stirred ionic bath, as disclosed in WO 93/21906.

1. Solvent Evaporation

Methods for forming microspheres using solvent evaporation techniques are described in E. Mathiowitz et al., J. Scanning Microscopy, 4:329 (1990); L. R. Beck et al., Fertil. Steril., 31:545 (1979); and S. Benita et al., J. Pharm. Sci., 73:1721 (1984), the disclosures of which are incorporated herein by reference. The polymer is dissolved in a volatile organic solvent, such as methylene chloride. A substance to be incorporated is added to the solution, and the mixture is suspended in an aqueous solution that contains a surface active agent such as poly(vinyl alcohol). The resulting emulsion is stirred until most of the organic solvent evaporated, leaving solid microspheres. Microspheres with different sizes (1-1000 microns) and morphologies can be obtained by this method. This method is useful for relatively stable polymers like polyesters and polystyrene. However, labile polymers, such as polyanhydrides, may degrade during the fabrication process due to the presence of water. For these polymers, some of the following methods performed in completely anhydrous organic solvents are more useful.

2. Hot Melt Microencapsulation

Microspheres can be formed from polymers such as polyesters and polyanhydrides using hot melt microencapsulation methods as described in Mathiowitz et al., Reactive Polymers, 6:275 (1987), the disclosure of which is incorporated herein by reference. In this method, the use of polymers with molecular weights between 3-75,000 daltons is preferred. In this method, the polymer first is melted and then mixed with the solid particles of a substance to be incorporated that have been sieved to less than 50 microns. The mixture is suspended in a non-miscible solvent (like silicon oil), and, with continuous stirring, heated to 5° C. above the melting point of the polymer. Once the emulsion is stabilized, it is cooled until the polymer particles solidify. The resulting microspheres are washed by decantation with petroleum ether to give a free-flowing powder. Microspheres with sizes between one to 1000 microns are obtained with this method.

3. Solvent Extraction

This technique is described, for example, in PCT WO 93/21906. The substance to be incorporated is dispersed or dissolved in a solution of the selected polymer in a volatile organic solvent like methylene chloride. This mixture is suspended by stirring in an organic oil, such as silicon oil, to form an emulsion. Microspheres that range between 1-300 microns can be obtained by this procedure.

4. Spray-Drying

Methods for forming microspheres using spray drying techniques are described in U.S. Pat. No. 6,262,034. The polymer is dissolved in an organic solvent such as methylene chloride. A known amount of a substance to be incorporated is suspended (insoluble agent) or co-dissolved (soluble agent) in the polymer solution. The solution or the dispersion then is spray-dried. Microspheres typically ranging between 1-10 microns are obtained.

5. Phase Inversion

Microspheres can be formed from polymers using a phase inversion method wherein a polymer is dissolved in a good solvent, fine particles of a substance to be incorporated, such as a drug, are mixed or dissolved in the polymer solution, and the mixture is poured into a strong non-solvent for the polymer, to spontaneously produce, under favorable conditions, polymeric microspheres, wherein the polymer is either coated on the particles or the particles are dispersed in the polymer. The method can be used to produce microparticles in a wide range of sizes, including, for example, about 100 nanometers to about 10 microns. Exemplary polymers which can be used include polyvinylphenol and polylactic acid. Substances which can be incorporated include, for example, imaging agents such as fluorescent dyes, or biologically active molecules such as proteins or nucleic acids.

6. Low Temperature Casting of Microspheres

Methods for very low temperature casting of controlled release microspheres are described in U.S. Pat. No. 5,019,400 to Gombotz et al. A polymer is dissolved in a solvent together with a dissolved or dispersed substance to be incorporated, and the mixture is atomized into a vessel containing a liquid non-solvent at a temperature below the freezing point of the polymer-substance solution, which freezes the polymer droplets. As the droplets and non-solvent for the polymer are warmed, the solvent in the droplets thaws and is extracted into the non-solvent, resulting in the hardening of the microspheres.

7. Double Walled Microcapsules

In one embodiment of a method for preparing multiwall polymer microspheres, two hydrophilic polymers are dissolved in an aqueous solution. A substance to be incorporated is dispersed or dissolved in the polymer solution, and the mixture is suspended in a continuous phase. The solvent then is slowly evaporated, creating microspheres with an inner core formed by one polymer and an outer layer of the second polymer. The continuous phase can be either an organic oil, a volatile organic solvent, or an aqueous solution containing a third polymer that is not soluble with the first mixture of polymers and which will cause phase separation of the first two polymers as the mixture is stirred.

Multilayer polymeric delivery devices can be prepared from two or more hydrophilic polymers using the method. Any two or more different biodegradable, or non-degradable, water soluble polymers which are not soluble in each other at a particular concentration as dictated by their phase diagrams may be used. Microspheres containing a polymeric core made of a first polymer and a uniform coating of a second polymer, and a substance incorporated into at least one of the polymers, can be made as described in U.S. Pat. No. 4,861,627.

C. Implantable Microchips

Polymeric microchips for multi-dose delivery are described by Richards, et al., Nat Mater. (2003) 2(11):709-10 and Kim, et al. J Control Release. (2007) 123(2):172-8. Biodegradable polymeric microchips can be fabricated as described in these studies for release of active over an extended period, for example, 142 day. As described in these papers, the microchips were 1.2 cm in diameter, 480-560 microm thick and had 36 reservoirs that could each be filled with a different chemical. The devices were fabricated from poly(L-lactic acid) and had poly(D,L-lactic-co-glycolic acid) membranes of different molecular masses covering the reservoirs.

A drug delivery system can be designed to release pulses of different drugs at intervals after implantation in a patient by using different molecular masses or materials for the membrane. The devices can also be designed to have differential degradation rates in vivo and in vitro, using different polymer composition and/or molecular weights, such as biocompatible poly(lactic acid) and poly(glycolic acid) homo- and co-polymers for a polymeric drug-delivery microchip. See U.S. Pat. Nos. 6,491,666, 6,527,762, 6,976,982, 7,226,442, and 7,604,628. Suitable devices can be obtained from Microchips Biotech.

IV. Kits

In a typical embodiment, an effective dosage unit is provided in a blister pack or sterile sealed container for use by a surgeon after resecting the tumor. Particles can be provided in lyophilized form in a container, where the particles are resuspended at the time of administration.

Kits can be provided containing a plurality of local delivery forms, in a variety of shapes, and loaded with pre-determined amounts of acriflavine, or acriflavine with additional chemotherapeutic or other agents.

The kits can also include sterile delivery catheters, syringes and needles for administering the local delivery forms.

V. Methods of Using

The local delivery forms are administered locally to a subject at a site in need of treatment.

A. Administration

Administration of the local delivery forms may be by implantation following an open surgery, or via a minimally invasive injection or insertion. Administration typically places the composition close to the tumor, onto the tumor, or at a resected tumor site.

B. Dosages and Administration Regimes

Any number of the local delivery forms may be administered at a time. The number of local delivery forms will vary dependent on the dosage of an agent needed to treat a disease. For example, 1, 2, 5, or 10 local delivery forms, each containing 10 mg of an active agent, may be administered to a site of a resected tumor for sustained release of an effective dose of 10 mg, 20 mg, 50 mg, or 100 mg of the active agent, respectively. Alternatively, one local delivery form containing 10 mg, 20 mg, 50 mg, or 100 mg of the active agent may be administered to deliver an effective dose of 10 mg, 20 mg, 50 mg, or 100 mg of the active agent, respectively. Therefore, an effective dose of an active agent may be delivered by altering the number of administered local delivery forms, by altering the amount of the agent in each of the local delivery forms, or both. The effective amount of the active agent may be released over a period of 2-3, weeks to 3-6 months.

The effective dosages can be determined by those skilled in the art based on the known pharmacokinetics of the drugs, prior studies using GLIADEL®, and animal studies such as those described herein. In some embodiments, an effective dosage is an amount of an active agent effective to reduce tumor size by about 10%, 15%, 20%, 25%, 30%, 35%, 40%, 45%, 50%, 55%, 60%, 65%, 70%, 75%, 80%, 85%, 90% or 95%. In some embodiments, the effective dosage is an amount of an active agent effective to prolong the median survival of the subject by about 15 days, 30 days, 1.5 months, 2 months, 2.5 months, 3 months, 3.5 months, 4 months, 4.5 months, 5 months, 5.5 months, 6 months, 6.5 months, 7 months, 7.5 months, 8 months, 8.5 months, 9 months, 9.5 months, 10 months, 10.5 months, 11 months, 11.5 months, 1 year, 1.5 years, 2 years, 3 years, 4 years, or 5 years relative to treatment with systemic chemotherapy.

In a preferred embodiment, the subject is also treated using standard techniques for radiation treatment of cancer patients, especially those with GBM. See, for example, Chang, et al., JAMA 293(20):557-564 (2005); Raza, et al. Expert Opin. Biol. Ther. 5(4):477-494 (2005), and Castro, et al. Pharmacol. Ther. 98(1):71-108 (2003).

C. Disease to be Treated

The local delivery forms are applied to organs or tissues of a subject in need of treatment. Typically, the subject in need of treatment has cancer with primary tumors, de novo tumors, secondary tumors, or tumor metastases. The tumors are typically solid tumors, such as sarcomas, carcinomas, and lymphomas. In preferred embodiments, the tumors to be treated are brain tumors.

Brain tumors may be primary, metastatic, malignant, or benign. Brain tumors account for 85% to 90% of all primary central nervous system (CNS) tumors. In general, the incidence of primary CNS tumors is higher in whites than in blacks, and mortality is higher in males than in females. Primary brain tumors include the following in decreasing order of frequency: anaplastic astrocytomas and glioblastomas (38% of primary brain tumors), meningiomas and other mesenchymal tumors (27% of primary brain tumors), pituitary tumors, schwannomas, CNS lymphomas, oligodendrogliomas, ependymomas, and low-grade astrocytomas, and medulloblastomas. Primary spinal tumors include the following in decreasing order of frequency: schwannomas, meningiomas, and ependymomas (79% of primary spinal tumors), sarcomas, astrocytomas, vascular tumors, and chordomas.

Glioblastoma Multiforme (GBM) is a fast-growing type of malignant brain tumor that is the most common brain tumor in adults. In 2010, more than 22,000 Americans were estimated to have been diagnosed and 13,140 were estimated to have died from brain and other nervous system cancers. 1 GBM accounts for about 15 percent of all brain tumors and occurs in adults between the ages of 45 to 70 years. Patients with GBM have a poor prognosis with median survival of less than 15 months following diagnosis. Currently there are no effective long-term treatments for this disease.

The present invention will be further understood by reference to the following comparative examples.

EXAMPLES

Example 1. Acriflavine Cytotoxicity In Vitro

Materials and Methods

The cytotoxicity of ACF was analyzed in rodent 9 L gliosarcoma (obtained from the Brain Tumor Research Center, University of California at San Francisco) and F98 glioma (a gift from R. Barth, Ohio State University) cell lines as well as in commercial and primary human glioblastoma cell lines, U87 (ATCC) and GB1A, respectively. The cells were plated in 96-well plates at a density of $4\times10^3$ cells/well, cultured for 24 h and treated with ACF (concentration range of 0.2 μM-25 μM). After co-incubation with ACF in medium for 24 h, cell growth was assessed using a CCK-8 assay (Dojindo, Kumamoto, Japan) according to manufacturers' protocol. Data are shown as mean+/−SEM and the inhibitory concentration 50% (IC50)+95% confidence interval and $R^2$ are reported.

The following concentrations of acriflavine: 0.0249 μM, 0.1245 μM, 0.249 μM, 2.5 μM, 25 μM, 50 μM, 500 μM, and 1000 μM were tested. CCK-8 assay was added to the wells, and the optical density was read at 450 nm by a microplate reader.

Results

The in vitro data showed that ACF inhibited proliferation in all glioma cell lines tested in a dose-dependent manner The IC50 concentration of acriflavine was found to be 1.07 μM on 9 L rat glioma cells ($R^2$=0.914) (FIG. 1).

Example 2. Local In Vivo Delivery of ACF Provides 100% Survival

Materials and Methods

As described by Sipos, et al. *Cancer Chemotherapy & Pharmacology*, 39(5):383-389, 1997. PMID 9054951, the ACF-p[CPP:SA, 20:80] wafers were prepared as follows. The CPP:SA copolymer was synthesized from 1,3-bis-(p-carboxyphenoxy propane) (CPP) and sebacic acid (SA) at a molar ratio of as 20:80 as described in Chasin et al., *Biopharm Manufact*, 1:33 (1988). Disk-shaped polymer implants (3 mm diameter, 1 mm height, 10 mg each) were prepared by melt mixing ACF powder into the melted polymer at 70° C. for 30 s and casting the uniform mixture into a 1-mm thick film. The film was cut into disks by means of a 3-mm bore.

Rats were implanted with 9 L tumor, an experimental glioma model characterized for its aggressive and rapid pattern of growth. Efficacy of locally delivered acriflavine via polymer wafer was tested in vivo on the 9 L tumor bearing rats. For polymer delivery, acriflavine was incorporated into an 10 mg implantable polyanhydride CPP:SA polymer at different concentration ratios of ACF/PCPP:SA, such as 5% (0.5 mg ACF), 10% (1 mg ACF), 25% (2.5 mg ACF), and 50% (5 mg ACF Rats were implanted with 9 L tumors at Day 0 and divided into the experimental group (n=12) and the control (n=16). In the experimental group each animal was treated with one wafer containing a 10% or 50% loaded ACF/PCPP:SA polymer delivered on Day 0 in the tumor cavity.

The animal surgery and tumor implantation were performed as described in Sipos, et al. 1997.

Specifically, male Fischer 344 rats weighing 200-250 g were obtained from Harlan Sprague-Dawley (Indianapolis, Ind.) and kept in accordance with the policies and principles of laboratory animal care of the Johns Hopkins School of Medicine Animal Care and Use Committee. Stereotactic injection of 9 L gliosarcoma pieces into the left parietal lobe of the rats was carried out as described by Judy et al., *J Neurosurg*, 82:103 (1995). The implantation of these tumor pieces resulted in the formation of intracranial tumors which, if untreated, were uniformly fatal in 12-14 days in the untreated animals.

All the animals enrolled in the efficacy studies were closely monitored for signs of toxicity, including failure to thrive and neurological deficits, every day for at least 120 days and then periodically after 120 days. Survival was assessed, and the brains of untreated as well as of treated animals were removed and preserved in 10% formalin for histological analysis.

Results

Figure 2:
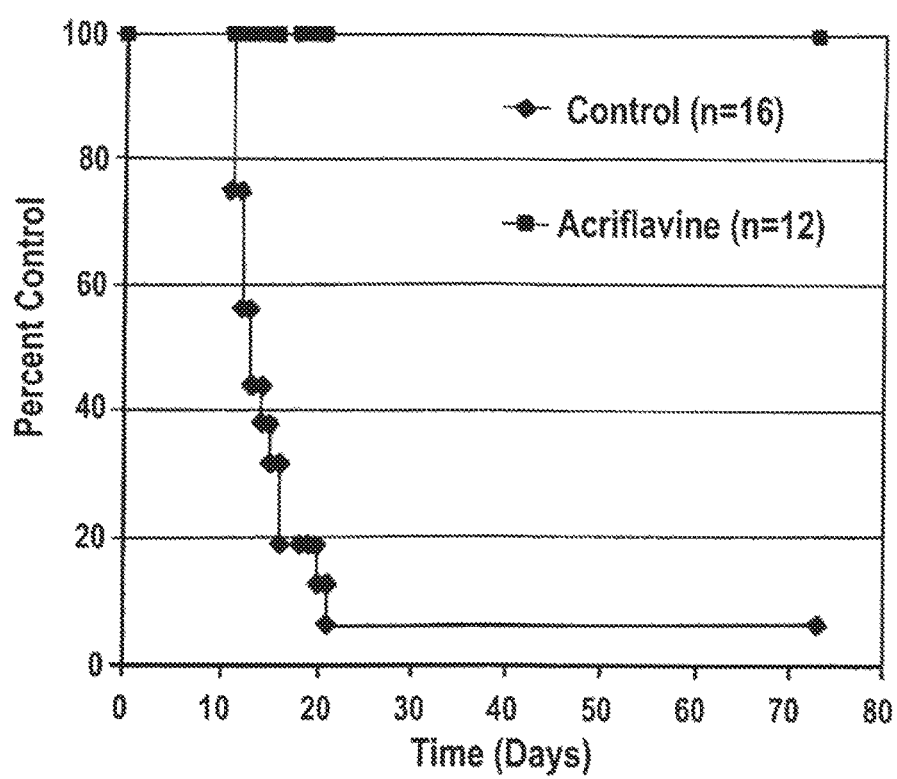
FIG. 2 is a line graph of percent survival (%) of control rats and rats with 25% ACF wafer (wafer containing 2.5 mg ACF) over time (days) (Kaplan-Meier survival curve). The median survival of the control animals was between 11 and 12 days. The rats treated with local acriflavine had 100% survival after 120 days (P<0.0001 vs control).

The 12 rats implanted with acriflavine wafers showed 100% survival after 120 days, while the median survival of the control was 11 to 12 days (P<0.0001 vs. control, FIG. 2).

Local delivery of acriflavine via polymer appeared very effective for rats with GBM. Acriflavine wafers were composed of polyanhydride poly[1,3-bis (carboxyphenoxy) propane-co-sebacic-acid] (CPP:SA), specifically, the formulation system of CPP:SA (20:80. The acriflavine/CPP:SA formulation provided effective and sustained release of the drug in the brain after local implantation. Systemic delivery may pose a risk due to the acriflavine accumulating in the liver.

The safety and efficacy of intracranially implanted ACF biodegradable wafers, used in monotherapy in an experimental glioma model is demonstrated. This local implantation of ACF achieved an extraordinary 100% survival rate of up to 120 days (p<0.0001), whereas the systemically administered ACF provided no survival benefit compared to the control (Example 3). These studies showed that interstitial local therapy via biodegradable polymer represents an effective strategy for the potential use of ACF in brain tumor therapy.

Example 3. Systemic In Vivo Delivery of ACF has No Efficacy in Brain Tumor Treatment Materials and Methods Several in vivo studies were performed to evaluate the efficacy of locally delivered ACF compared to systemic ACF, and assess the efficacy of ACF polymers at decreasing ACF concentrations compared to untreated animals, animals receiving empty polymers and animals that received the commonly used chemotherapy for glioblastoma, temozolomide (TMZ).

A toxicity study was performed to assess the maximally tolerated dose (MTD) of systemic ACF in Fisher 344 (F344) rats. Groups of animals received escalating dosages of ACF given intraperitoneally. All animals were weighed every 3 days during the treatment and monitored for clinical signs of systemic toxicity up to 30 days post-treatment.

Efficacy studies were conducted to evaluate the effect of systemically delivered ACF on animals bearing intracranial brain tumors. This efficacy was compared to the efficacy of locally delivered ACF polymers at a loading concentration of 50% ACF polymer (5 mg ACF in a 10 mg polymerA total of 44 rats were intracranially implanted with 9 L tumor pieces as previously described (Recinos et al., *Neurosurgery*, 66:530-537 (2010)) and randomized into 4 groups: controls which received no treatment; a group that received Local 50% ACF simultaneous with tumor implantation on Day 0; and two groups that received systemic ACF (5 mg/kg/daily) up to death, that started either on Day 0 or on Day 5. Long term survivors (LTS) were defined as animals that lived at least 120 days after tumor implantation.

Results

Figure 3:
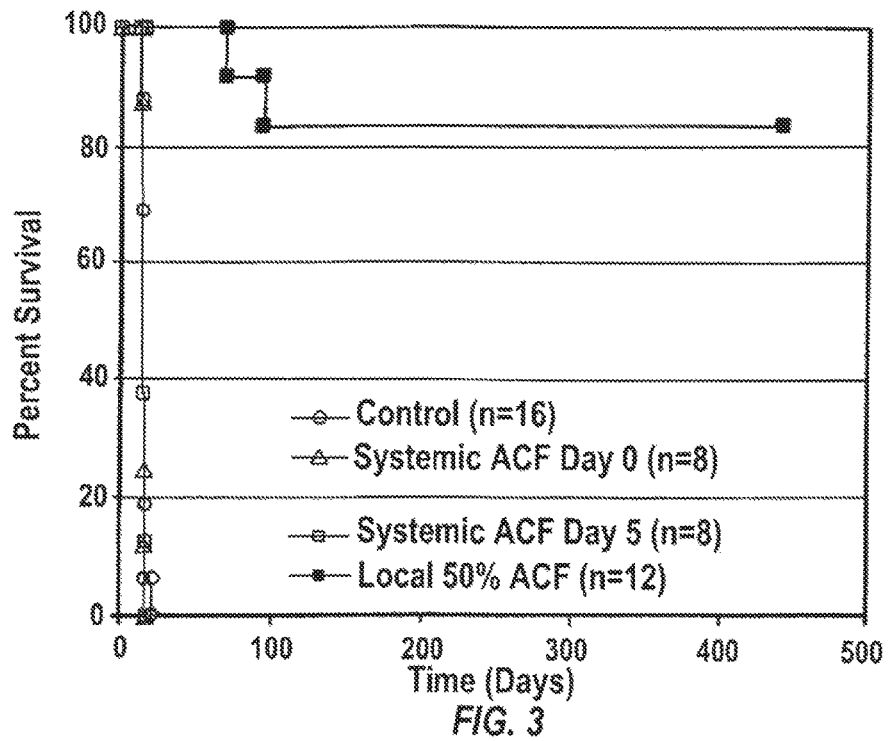
FIG. 3 is a line graph of percent survival (%) of F344 rats implanted with 9 L gliosarcoma in various treatment groups over time (days) (Kaplan-Meier survival curve). The treatment groups were: control (●), n=16; systemic ACF day 0 (▲), n=8; systemic ACF day 5 (■), n=8; and local 50% ACF (-■-), n=12.

Systemically delivered ACF, either first administered on Day 0 or on Day 5 after tumor implantation, provided no benefit in survival compared to the control (median of 14 days vs. median of 13.5 days), respectively (FIG. 3). Over 80% of animals treated with local acriflavine polymer survived past 400 days following tumor implantation.

Example 4. Local In Vivo Delivery of ACF Shows a Dose-Dependent Increase in Survival of Rats with 9 L Gliosarcoma Materials and Methods An efficacy study was performed to assess further decreasing dosages of ACF compared to both untreated animals and animals treated with empty polymers on Day 0. A total of 50 rats were implanted with 9 L gliosarcoma and randomized among 4 groups receiving either no treatment, or intracranial implantation of either empty (0%) (0 mg ACF), 10% ACF (1 mg ACF) or 25% ACF (2.5 mg ACF) polymers by weight on Day 0. One single polymer (10 mg) was intracranially implanted on Day 0.

Results

Figure 4:
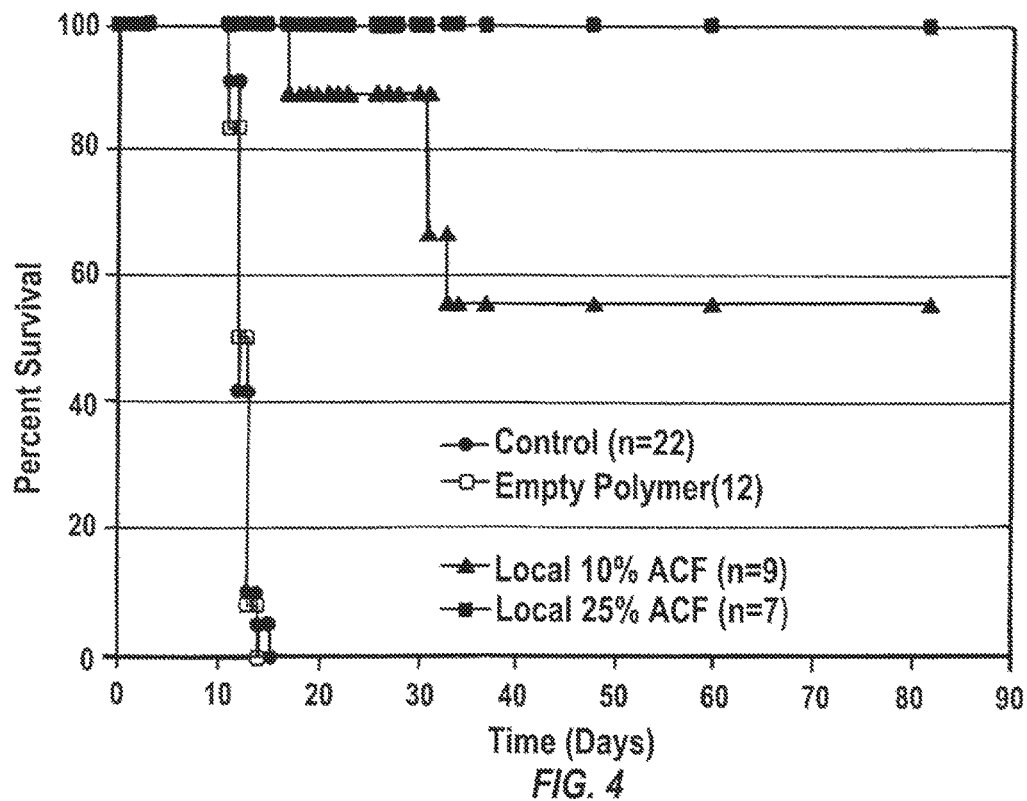
FIG. 4 is a line graph of percent survival (%) of F344 rats implanted with 9 L gliosarcoma in various treatment groups over time (days) (Kaplan-Meier survival curve). The treatment groups were: control (●), n=22, empty polymer (□), n=12; local 10% ACF (▲), n=9, and local 25% ACF (■), n=7.

Locally delivered 10% ACF polymer showed a significantly longer median survival compared to those animals that were either untreated or those that received empty polymer (p<0.0001) with 50% long term survivors (FIG. 4).

Animals receiving local ACF polymers, at both 50% and 25% loading dosages, consistently showed a significantly improved median survival compared to the control group (p<0.0001, FIGS. 3 and 4) with 80%-100% of the local 50% or 25% ACF-polymer treated animals showing long term survival beyond 1 year in all the efficacy studies except for 3 cases out of a total of 28 rats of relapsed tumor.

Example 5. Local Dosage Form Delivery of Acriflavine is More Efficacious at Increasing Survival than an Oral Daily Treatment with Temozolomide Materials and Methods An efficacy study was also conducted to compare the treatment with 25% of ACF polymer to that with oral temozolomide. A total of 32 rats were implanted with 9 L gliosarcoma and randomized among 3 groups that received either no treatment, 50 mg/kg/day of oral temozolomide from Days 5-9, or intracranial implantation on Day 0 of 25% ACF polymer.

Results

Figure 5:
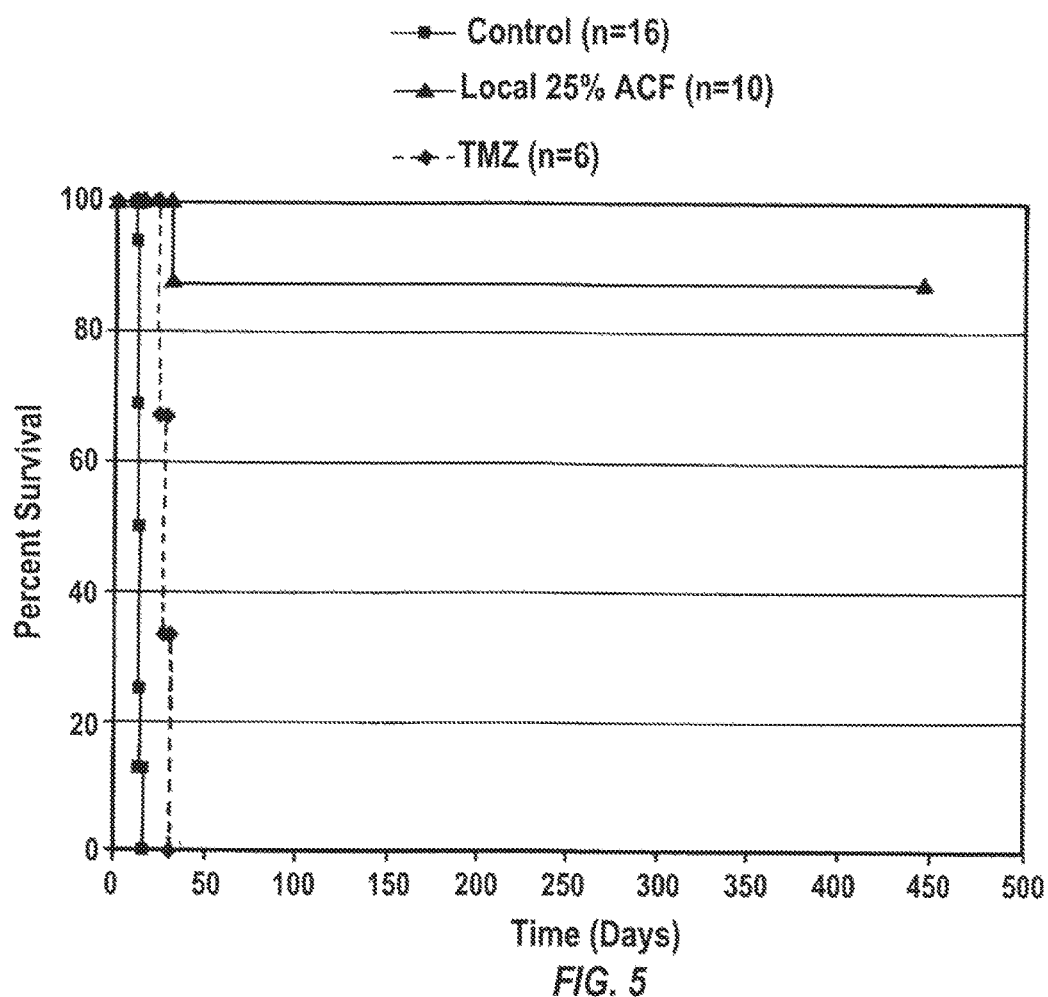
FIG. 5 is a line graph of percent survival (%) of F344 rats implanted with 9 L gliosarcoma in various treatment groups over time (days) (Kaplan-Meier survival curve). The treatment groups were: control (■), n=16; local 25% ACF (▲), n=10; and temozolomide (TMZ) (♦), n=6.

The local implantation of ACF wafers significantly prolonged survival compared to untreated controls (median survival was 13 days), and groups treated with systemically delivered temozolomide (median survival was 28 days) (FIG. 5). Over 80% of the 25% ACF polymer treated animals survived past 400 days after tumor implantation

Example 6. MRI Monitoring and Histological Assessment Reveals Absence of Tumor Mass or Viable Tumor Cells in Animals Treated with ACF Wafer Materials and Methods The animals enrolled in the efficacy study of Example 4 were monitored using T1-weighted MRI at 5 follow-up time points.

Serial coronal and axial images pre- and post-Gadolinium administration were performed in all animals at 2, 7 and 15 days post-implantation. The animals treated with local 25% ACF and 10% ACF were imaged also at later time points such as after 30 and 60 days post-implantation.

Histological examination of coronal sections of rat brains was performed using Hematoxylin and Eosin (H&E) staining. The coronal sections were from rats without treatment, and those treated with local 10% ACF or local 25% ACF. The rat brains were collected at 7, 15 and 60 days post tumor implantation.

Results

Both MRI follow-up and neuropathological examination, the latter conducted by two independent and blinded neuropathologists, confirmed the presence of a tumor mass in all untreated animals, whereas the brains imaged and then harvested from the animals that received either local 10% ACF polymer or 25% ACF polymer showed a surgical cavity without tumor mass, with visible debris of polymer, some inflammatory reaction, and without viable tumor cells.

H&E images taken within 1.5 mm around the tumor implantation site showed that the control animals had an extensive tumor mass at 7 and 15 days post tumor implantation. In the sections of treated animals, at 7, 15, and 60 days, the images showed the surgical cavity without tumor mass, with no viable tumor cells, and presence of fragments of ACF wafers with local 10% ACF or local 25% ACF treatment.

These studies showed that interstitial local therapy with ACF delivered via biodegradable polymer represents an effective strategy for the potential use of local dosage forms of ACF in brain tumor therapy and described the high efficacy of the local dosage forms of ACF in the treatment of brain tumors.

We claim:

1. A method of treating an individual with a solid tumor comprising administering a composition comprising acriflavine or its derivatives in a local delivery formulation for controlled local administration of an effective amount of the acriflavine or its derivatives to the tumor, onto the tumor, or at a resected tumor site, to reduce tumor size and/or, prolong survival of the individual;

wherein the local delivery formulation does not produce systemic level of the acriflavine or its derivatives producing unacceptable side effects;

wherein the solid tumor is a brain tumor; and wherein the local delivery formulation is in the form of a polymeric implant, polymeric particles or a microchip.

2. The method of claim 1, wherein the effective amount of acriflavine or its derivatives is released over a period of 1, 2, 3, 4, 5, 6, 7, 8, 9, 10 or more weeks.

3. The method of claim 1 further comprising administering additional anti-cancer therapies to the subject.

4. The method of claim 1, wherein the composition is administered to the subject at an area close to the tumor.

5. The method of claim 1, wherein the composition is administered to the subject at an area of a resected tumor.

* * * * *